US012667827B2

(12) United States Patent
Wang et al.

(10) Patent No.: US 12,667,827 B2
(45) Date of Patent: Jun. 30, 2026

(54) COPPER ALUMINUM CATALYST USED FOR 1,4-BUTYNEDIOL PRODUCTION

(71) Applicant: BASF CORPORATION, Florham Park, NJ (US)

(72) Inventors: Huan Wang, Shanghai (CN); Ai Ling Lv, Shanghai (CN); Diana Carolina Galeano Nunez, Shanghai (CN); Mario Soorholtz, Shanghai (CN)

(73) Assignee: BASF Corporation, Florham Park, NJ (US)

( * ) Notice: Subject to any disclaimer, the term of this patent is extended or adjusted under 35 U.S.C. 154(b) by 497 days.

(21) Appl. No.: 18/022,817

(22) PCT Filed: Jun. 10, 2021

(86) PCT No.: PCT/CN2021/099418
§ 371 (c)(1),
(2) Date: Feb. 23, 2023

(87) PCT Pub. No.: WO2022/041927
PCT Pub. Date: Mar. 3, 2022

(65) Prior Publication Data
US 2023/0311100 A1 Oct. 5, 2023

(30) Foreign Application Priority Data
Aug. 25, 2020 (CN) .......................... 202010863828.5

(51) Int. Cl.
*B01J 23/843* (2006.01)
*B01J 21/04* (2006.01)
(Continued)

(52) U.S. Cl.
CPC ........... *B01J 23/8437* (2013.01); *B01J 21/04* (2013.01); *B01J 23/002* (2013.01); *B01J 37/035* (2013.01); *C07C 29/42* (2013.01); *B01J 35/40* (2024.01)

(58) Field of Classification Search
CPC ...... B01J 23/8437; B01J 21/04; B01J 23/002; B01J 37/035; B01J 35/40; C07C 29/42; C07C 33/046
See application file for complete search history.

(56) References Cited

U.S. PATENT DOCUMENTS 3,920,759 A 11/1975 Hort
4,110,249 A 8/1978 Fremont
(Continued)

FOREIGN PATENT DOCUMENTS

CN 105622336 A 6/2016
CN 109772351 A 5/2019
(Continued)

OTHER PUBLICATIONS

International Search Report and Written Opinion for PCT/CN2021/099418 mailed Sep. 8, 2021, 8 pages.
(Continued)

*Primary Examiner* — Jafar F Parsa
(74) *Attorney, Agent, or Firm* — Element IP, PLC

(57) ABSTRACT
The present invention is generally related to a novel catalytic composition and a method for the production of 1,4 -butyne-diol by catalytic ethynylation of formaldehyde, the said method is known as the Reppe reaction. The invented catalyst with lower copper content would provide an advantageous combination of improved utilization efficiency of copper, reduced copper leaching and enhanced filterability, and has minimal to no impact on catalytic activity.

12 Claims, 2 Drawing Sheets

(51) Int. Cl.

| | | |
|---|---|---|
| *B01J 23/00* | (2006.01) | |
| *B01J 35/40* | (2024.01) | |
| *B01J 37/03* | (2006.01) | |
| *C07C 29/42* | (2006.01) | |

(56) References Cited

U.S. PATENT DOCUMENTS

| | | | |
|---|---|---|---|
| 9,006,129 B2 | 4/2015 | Madon | |
| 10,537,886 B2 | 1/2020 | Madon | |
| 2018/0236439 A1* | 8/2018 | Madon | ................... B01J 27/232 |

FOREIGN PATENT DOCUMENTS

| | | | |
|---|---|---|---|
| CN | 110876939 A | 3/2020 | |
| CN | 111939919 A | 11/2020 | |
| WO | WO-2016/160921 A1 | 10/2016 | |

OTHER PUBLICATIONS

European Search Report for EP Patent Application No. 21859771.4, Issued on Jul. 26, 2024, 3 pages.

* cited by examiner

COPPER ALUMINUM CATALYST USED FOR 1,4-BUTYNEDIOL PRODUCTION

CROSS REFERENCE TO RELATED APPLICATION(S)

The present application is a national stage entry under 35 U.S.C. § 371 of International Application No. PCT/CN2021/099418, filed on Jun. 10, 2021, which claims priority to Chinese Patent Application No. 202010863828.5, filed on Aug. 25, 2020, the entire contents of which are incorporated herein by reference in their entirety.

FIELD OF THE INVENTION

The present invention is generally related to a novel catalytic composition and a method for the production of 1,4-butynediol by catalytic ethynylation of formaldehyde, the said method is known as the Reppe reaction. The invented catalyst with lower copper content would provide an advantageous combination of improved utilization efficiency of copper, reduced copper leaching and enhanced filterability, and has minimal to no impact on catalytic activity.

BACKGROUND OF THE INVENTION 1,4-butynediol (BYD), is an important organic compound intermediate and forms derivatives with various chemicals. In recent years, high growth of the hydrogenation product 1,4-butanediol (BDO) and its downstream products, i.e., gamma-butyrolactone (GBL), tetrahydrofuran (THF), polybutylene terephthalate (PBT) and polyurethane (PU), raises an increase in demand of 1,4-butynediol. Industrial process to produce 1,4-butynediol is mainly by ethynylation reaction of formaldehyde and acetylene via coal chemical industry. There is abundant coal resource which makes the production of via coal-chemistry route has unique advantages and much lower cost.

The state of art production of 1,4-butynediol in China is conducted via ethynylation in the slurry-phase reactor, which decreases operation pressure and risk of explosion compared to fixed-bed reactor under high pressure in the last century. Typically, the catalyst is a solid powder in micron scale containing copper oxide, bismuth oxide and siliceous material. For example, the preparation and its application of copper/bismuth oxide catalyst on magnesium silicate carrier and with silica binder was disclosed by U.S. Pat. No. 9,006,129B2 and U.S. Ser. No. 10/537,886B2, separately. However, one drawback of this kind of catalyst is the leaching of silica along with the catalytic reaction. The leached silica in product solution is detrimental to the following hydrogenation of 1, 4-butynediol catalyzed by nickel. Generally, the silica needs to be removed from product solution by an ion-exchanger, which normally produces large quantities of wastewater and causes high cost to deal with.

CN 110876939A discloses a preparation process of ethynylation catalyst on alumina carrier which contains no silica. The prepared catalyst shows significantly lower leaching of silica compared to commercial catalyst. But the content of copper oxide in disclosed examples is relatively higher than the level of commercial catalyst in order to reach the comparable activity. Higher copper oxide content would increase the possibility of leaching of copper and cause severe accumulation of polymeric species inevitably formed along with long-term operation, which would block the active site and arise higher risk because of its flammability.

Copper acetylide, derived from copper oxide, is considered to be the active species for the ethynylation reaction. Reducing copper content in catalyst would be an attractive approach to lower operation risk if the catalytic activity could be retained in the comparable level. Cu/Bi ratio would be also adjusted in order to achieve well catalytic activity and filterability at the same time.

SUMMARY OF THE INVENTION

The object of this invention is to provide a Reppe reaction catalytic composition with improved catalytic activity and filterability, which comprises lower amount of copper species compared to commercial catalyst.

In one aspect, a catalytic composition is provided, wherein the catalytic composition comprises from 5% to 35% by weight of Cu, calculated as CuO; from 0.1% to 7% by weight of Bi, calculated as $Bi_2O_3$; from 60% to 95% by weight of Al, calculated as $Al_2O_3$.

In another aspect, a process for producing the catalytic composition described above is provided, wherein the process comprises 1) precipitation of a copper-containing and a bismuth-containing aqueous solution with precipitation agent, on a particulate carrier; 2) drying the treated particulate carrier and calcining at 300 to 800° C. to form the catalytic composition; wherein the particulate carrier comprises an aluminium source.

In another aspect, a process for using the catalytic composition described above for hydrogenation, dehydrogenation, hydrogenolysis, or ethynylation is provided.

The catalytic composition with lower copper content prepared in this invention is able to achieve comparable activity to commercial catalyst. Although its copper content is lower, the activity of catalyst retains in the same level and its copper oxide catalytic activity is higher compared to examples supported by alumina carrier disclosed in the prior art. In addition, the leached Cu in product solution for invented catalyst is much less than the ones in the prior art.

DETAILED DESCRIPTION OF THE INVENTION

Figure 1:
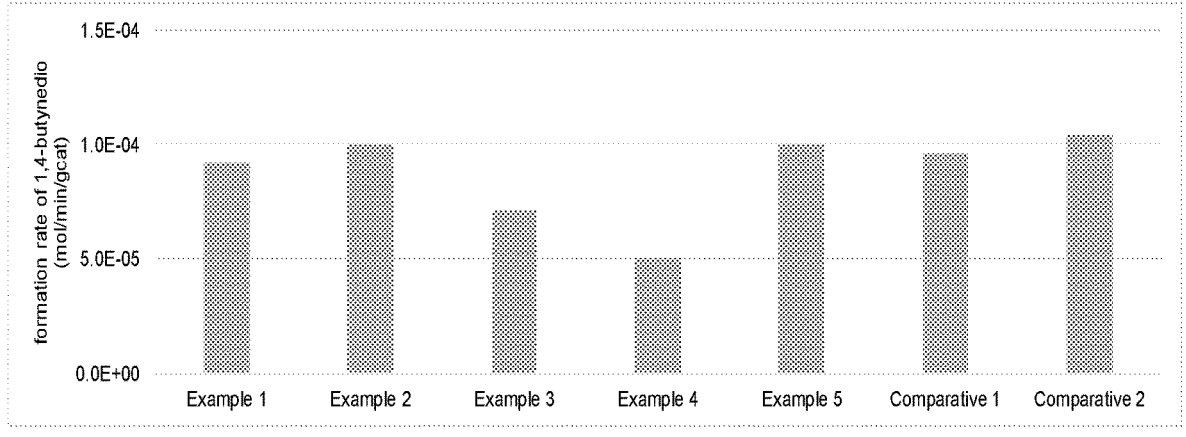
FIG. 1 shows a plot of comparison of formation rate of 1,4-butynediol per gram of catalyst.

Before describing several exemplary embodiments of the invention, it is to be understood that the invention is not limited to the details of construction or process steps set forth in the following description. The invention is capable of other embodiments and of being practiced or being carried out in various ways.

With respect to the terms used in this disclosure, the following definitions are provided.

Throughout the description, including the claims, the term "comprising one" or "comprising a" should be understood as being synonymous with the term "comprising at least one", unless otherwise specified, and "between" or "to" should be understood as being inclusive of the limits.

The terms "a", "an" and "the" are used to refer to one or to more than one (i.e., to at least one) of the grammatical object of the article.

The term "and/or" includes the meanings "and", "or" and also all the other possible combinations of the elements connected to this term.

All percentages and ratios are mentioned by weight unless otherwise indicated.

Thus, according to one aspect of the invention, provided is a catalytic composition comprising from 5% to 35%, preferably from 10% to 30%, more preferably 15% to 30%, and the most preferably 20 to 30%, including 25 and 28%, by weight of Cu, calculated as CuO; from 0.1% to 7%, preferably from 0.2% to 4%, including 0.4, 1.0, 1.5, 2.0, 2.5, 3.0 and 3.5%, by weight of Bi, calculated as $Bi_2O_3$; from 60% to 95%, preferably from 70% to 90%, including 75, 80 and 85%, by weight of Al, calculated as $Al_2O_3$.

In one or more embodiments, the Cu to Bi molar ratio is 55-300:1, preferably 80-200:1.

In one or more embodiments, the $Al_2O_3$ has a $D_{50}$ of between 0.1 to 20 μm, preferably 0.2 to 15 μm.

As used herein, "$D_{50}$" has its usual meaning of median diameter referring to the point where the portions of particles with diameters smaller and larger than this value are 50%. The particle size distribution is measured by using laser diffraction particle size analyzer.

In one or more embodiments, the catalytic composition has a $D_{50}$ of between 0.5 to 40 μm, preferably between 1 to 30 μm.

Another aspect includes methods for producing the catalytic composition described above, wherein the methods comprise steps of:

1) precipitation of an acidic copper-containing aqueous solution with precipitation agent, on a particulate carrier;

2) drying the treated particulate carrier and calcining at 300 to 800° C. to form the catalytic composition; wherein the particulate carrier comprises alumina.

A type of the alkaline aqueous solution used as the precipitation agent is not particularly limited, but inorganic alkalis such as aqueous solution of sodium hydroxide, an aqueous solution of potassium hydroxide and ammonium hydroxide, and the mixture thereof are generally used.

As used herein, the term "mixture" or "combination" refers, but is not limited to, a combination in any physical or chemical form, e.g., blend, solution, suspension, alloy, composite, or the like.

With reference to a copper source, typical copper sources may include, but not limited to, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, and the mixture thereof.

With reference to a bismuth source, typical bismuth sources may include, but not limited to bismuth chloride, bismuth oxychloride, bismuth bromide, bismuth silicate, bismuth hydroxide, bismuth trioxide, bismuth nitrate, bismuth subnitrate, bismuth oxycarbonate, and the mixture thereof.

Typical alumina used herein could be α-alumina, β-alumina, γ-alumina, and the mixture thereof.

Other aspects include methods for using the catalytic composition described above for hydrogenation, dehydrogenation, hydrogenolysis, or ethynylation.

Various embodiments are described hereinafter. It should be noted that the specific embodiments are not intended as an exhaustive description or as a limitation to the broader aspects discussed herein.

Preparation of the Catalyst

The particulate alumina carrier is first added to water in a precipitation vessel. An acidic solution is made up of a mixture of copper-containing and bismuth-containing salts in a separate vessel. A basic solution is made up of sodium hydroxide in a separate vessel. The temperature of the solution in the precipitation vessel is set at the precipitation temperature which is held constant throughout the precipitation process with a value anywhere from about 40° C. to about 90° C. The acid mixture and the sodium hydroxide solution are simultaneously added to the vessel containing water and the particulate carrier. The precipitation is carried out at a constant pH of about 7 to about 11. During precipitation, the flow of the acid solution is kept constant while the flow of the NaOH solution is adjusted to keep the precipitation pH constant. The time of precipitation may be anywhere from 15 mins to 120 mins. Usually the time is about 30 mins to about 60 mins. After the precipitation step, the precipitate may be aged for a short time, about 15 mins to about 120 mins. Afterwards, the precipitate is filtered, washed, and dried. The dried material is calcined in air. The calcination temperature may vary between about 300° C. to about 800° C., 400, 500, 600, and 700° C. included.

Catalytic Performance Testing of the Catalyst

By use of identical testing conditions according to U.S. Pat. No. 9,006,129B2, the active catalyst is preferably generated by means of the introduction of the acetylene into the formaldehyde-catalyst reaction medium. In the first reactor, the calcined catalyst is mixed with formaldehyde aqueous solution. The pH of the aqueous medium is adjusted to the range of 7.0 to 10.0, and preferably 8.0. The control of pH is to suppress the formation of formic acid, which will react with copper compound and raise loss of copper due to leaching into solution. Activation of the catalyst is conducted after acetylene stream is introduced and the reactor is heated from room temperature to about 80° C. The activation process generally requires 5 hours.

Afterwards, the slurry was removed, centrifuged, and decanted, leaving wet catalyst ready for activity testing. In the second reactor, a certain amount of wet catalyst is mixed with formaldehyde aqueous solution. Acetylene stream is then introduced with partial pressure generally from 0.5 to 1.9 atmospheres, preferably 1.0 atmosphere. catalyst will be present in amounts of about 1 to 20 weight parts per 100 weight parts of formaldehyde aqueous medium. The reactor is heated from room temperature to about 80° C. The reaction process generally requires 5 hours and the pH of aqueous medium after reaction is about 5.0. The product mixture is analyzed by gas chromatography in which butynediol (primary product) and propargyl alcohol (product intermediate) were quantified and the activity of catalyst is determined.

Filterability Testing of the Catalyst

For ethynylation process in plant, a filter is used for separation of spent catalysts and reaction products. In this way, spent catalysts are recycled, mixed with fresh catalyst and fed back into reactors. Therefore, the filtration speed of spent catalysts is critical to the recycling efficiency. The filtration rate is tested for the catalyst after attrition: about 4 g of fresh catalyst is added to 40 mL DI $H_2O$ and stirred at room temperature for a sufficiently long time. Afterwards, the slurry is filtered, and the time used for filtration is recorded to calculate the filtration rate accordingly.

The invention will be more specifically described and explained by means of the following examples, which are not to be considered as limiting but only illustrative of the invention. All parts and proportions therein as well as in the appended claims are by weight unless otherwise specified.

EXAMPLES

Example 1

α-alumina carrier with average particle size $D_{50}$ of 5 μm is added into water to obtain a 37 wt % slurry. 117.3 g of copper nitrate (contains 15.5 wt % Cu) and bismuth nitrate (Cu/Bi molar ratio as 95/1) solution are precipitated with 15 wt % sodium hydroxide solution onto the particulate carrier. After the precipitation step, the precipitate is aged at 35° C. for 10 mins. Afterwards, the precipitate is filtered and dried. The catalyst is obtained after calcination at 450° C. and its composition is shown in Table 1.

Example 2

α-alumina carrier with average particle size $D_{50}$ of 5 μm is added into water to obtain a 37 wt % slurry. 117.3 g of copper nitrate (contains 15.5 wt % Cu) and bismuth nitrate (Cu/Bi molar ratio as 190/1) solution are precipitated with 15 wt % sodium hydroxide solution onto the particulate carrier. After the precipitation step, the precipitate is aged at 35° C. for 10 mins. Afterwards, the precipitate is filtered and dried. The catalyst is obtained after calcination at 450° C. and its composition is shown in Table 1.

Example 3

α-alumina carrier with average particle size $D_{50}$ of 5 μm is added into water to obtain a 37 wt % slurry. 55.4 g of copper nitrate (contains 15.5 wt % Cu) and bismuth nitrate (Cu/Bi molar ratio as 190/1) solution are precipitated with 15 wt % sodium hydroxide solution onto the particulate carrier. After the precipitation step, the precipitate is aged at 35° C. for 10 mins. Afterwards, the precipitate is filtered and dried. The catalyst is obtained after calcination at 450° C. and its composition is shown in Table 1.

Example 4

α-alumina carrier with average particle size $D_{50}$ of 5 μm is added into water to obtain a 37 wt % slurry. 55.4 g of copper nitrate (contains 15.5 wt % Cu) and bismuth nitrate (Cu/Bi molar ratio as 48/1) solution are precipitated with 15 wt % sodium hydroxide solution onto the particulate carrier. After the precipitation step, the precipitate is filtered and dried. The catalyst is obtained after calcination at 450° C. and its composition is shown in Table 1.

Example 5

α-alumina carrier with average particle size $D_{50}$ of 14 μm is added into water to obtain a 37 wt % slurry. 117.3 g of copper nitrate (contains 15.5 wt % Cu) and bismuth nitrate (Cu/Bi molar ratio as 190/1) solution are precipitated with 15 wt % sodium hydroxide solution onto the particulate carrier. After the precipitation step, the precipitate is aged at 35° C. for 10 mins. Afterwards, the precipitate is filtered and dried. The catalyst is obtained after calcination at 450° C. and its composition is shown in Table 1.

Comparative Example 1

α-alumina carrier with average particle size $D_{50}$ of 5 μm is added into water to obtain a 26 wt % slurry. 117.3 g of copper nitrate (contains 15.5 wt % Cu) and bismuth nitrate (Cu/Bi molar ratio as 48/1) solution are precipitated with 15 wt % sodium hydroxide solution onto the particulate carrier. After the precipitation step, the precipitate was aged at 35° C. for 10 mins. Afterwards, the precipitate was filtered and dried. The catalyst was obtained after calcination at 450° C. and its composition is shown in Table 1.

Comparative Example 2

α-Alumina carrier with average particle size $D_{50}$ of 15 μm is added into 200 mL of water to obtain a slurry and heat it up to 60° C. Prepare 500 mL of 1 mol/L copper nitrate solution containing 10 g/L bismuth nitrate. Add 50 mL of Cu/Bi nitrate solution into the carrier slurry by use of peristaltic pump and keep stirring for 10 mins. Then add 1 mol/L sodium carbonate solution into the slurry to adjust pH of slurry to 7.0. Afterwards, add another 50 mL of Cu/Bi nitrate solution into the carrier slurry and keep stirring for 10 mins, followed by adding 1 mol/L sodium carbonate solution into the slurry to adjust pH of slurry to 7.0 again. Repeat above procedure until all of 500 mL of Cu/Bi nitrate solution is added. Afterwards, the precipitate is filtered, washed and dried. The catalyst is obtained after calcination at 400° C. for 4h and its composition is shown in Table 1.

Table 1 shows catalyst component in terms of CuO, $Bi_2O_3$ and $Al_2O_3$ as well as Cu/Bi molar ratio for Examples 1 to 5 and Comparative example 1 to 2.

TABLE 1

| Catalyst component data | | | |
| --- | --- | --- | --- |
| | CuO (wt %) | $Bi_2O_3$ (wt %) | $Al_2O_3$ (wt %) | Cu/Bi molar ratio |
| Example 1 | 27.2 | 0.8 | 72.0 | 95 |
| Example 2 | 27.3 | 0.4 | 72.3 | 190 |
| Example 3 | 15.1 | 0.2 | 84.6 | 179 |
| Example 4 | 15.0 | 0.9 | 84.0 | 48 |
| Example 5 | 27.3 | 0.4 | 72.3 | 190 |
| Comparative 1 | 37.8 | 2.3 | 59.9 | 48 |
| Comparative 2 | 50.9 | 4.1 | 44.8 | 36 |

Catalytic test was carried out in two steps. First the catalyst was activated to form the active copper acetylide on the surface of catalyst. It was then transferred to the reaction vessel. Detailed procedure is shown as following. The activation was conducted in the reactor containing 100 mL formalin (37 wt % formaldehyde aqueous solution). 1.5M sodium hydroxide solution was added to formalin to adjust initial pH to about 7.5-9.0 and 15 g of catalyst was then added to formalin after the adjust of pH. Inertization of the reactor was conducted by purging nitrogen and then gas flow was exchanged to acetylene with 80 mL/min. Start stirring and on-line control pH at ca. 8.0 via NaOH solution, and start heating up to 80° C. The reaction was kept for 5 hours. Afterwards, the reactor was cooled down to room temperature under gas flow of acetylene. Nitrogen was purged into reactor for inertization and the slurry was discharged, centrifuged, and decanted, leaving wet catalyst ready for activity testing. 0.8 g (dry basis) of catalyst was added into reactor with formaldehyde aqueous solution. Similarly, the initial pH of formalin was adjusted to 8.0 by sodium hydroxide solution. The flow rate of acetylene was kept constant at 50 mL/min and the reaction temperature was 80° C. After 5 hours, the reactor was cooled down under gas flow of acetylene followed by purging of nitrogen for inertization. The slurry was discharged and centrifuged. The product mixture is analyzed by gas chromatography in which butynediol and propargyl alcohol were quantified. A sodium sulfite titration method is used to determine the amount of formaldehyde remaining in the product. Thereafter, the activity of catalyst is evaluated by the formation rate of butynediol, which is calculated on the basis of reaction time of 300 min and catalyst mass of 0.8 g. Similar catalytic test was conducted for Example 2, Example 3, Example 5 and Comparative 2 but with longer reaction time of 40 hours. Afterwards, copper content in product solution was measured and the result is shown in Table 2.

Filterability test was conducted by simulating catalyst attrition in solution. About 4 g of fresh catalyst was added to about 40 mL DI $H_2O$. The stirring was started with a constant rate of 250 rpm and kept at room temperature for 24 hours, respectively. Afterwards, the slurry was filtered, and the time used for filtration was recorded to calculate the filtration rate accordingly with the unit of mL/min.

Figure 2:
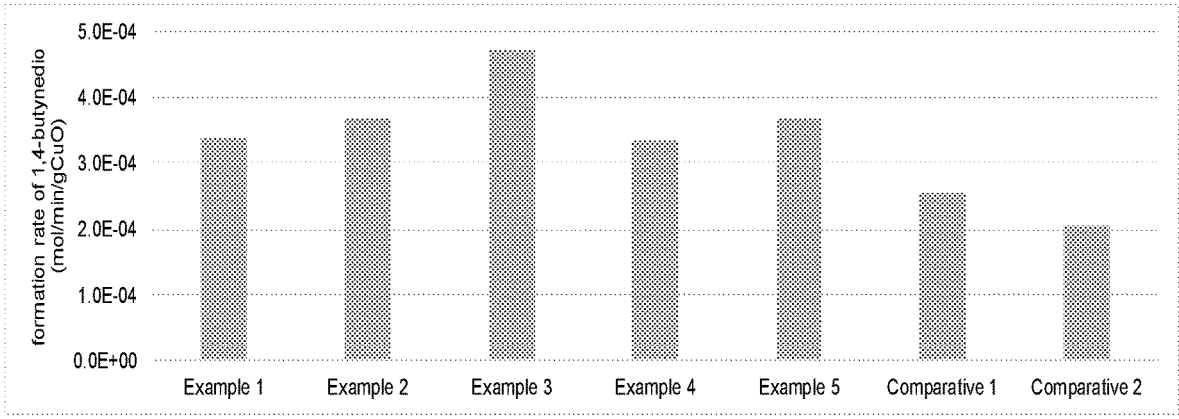
FIG. 2 shows a plot of comparison of formation rate of 1,4-butynediol per gram of CuO species in catalyst.

A comparison of catalytic activity per gram of catalyst and per gram of CuO for Examples and Comparative examples was provided in FIG. 1 and FIG. 2. It is shown that Examples with lower Cu content and higher Cu/Bi ratio have similar formation rate of 1,4-butynediol per gram of catalyst but higher CuO catalytic activity compared to Comparative Examples. This indicates higher utilization efficiency of active species for alumina supported CuO/$Bi_2O_3$ catalyst.

Lower Cu content for invented catalysts would have less Cu leaching possibility. As shown in Table 2, leached Cu in product solution after reaction time of 40 hours is reduced for invented catalysts compared to the sample in the prior art.

TABLE 2

| Comparison of leached Cu in product solution after 40 hours reaction | |
|---|---|
| | Cu content in product solution (ppm) |
| Example 2 | <10 |
| Example 3 | <10 |

TABLE 2-continued

| Comparison of leached Cu in product solution after 40 hours reaction | |
|---|---|
| | Cu content in product solution (ppm) |
| Example 5 | <10 |
| Comparative 2 | 57 |

Figure 3:
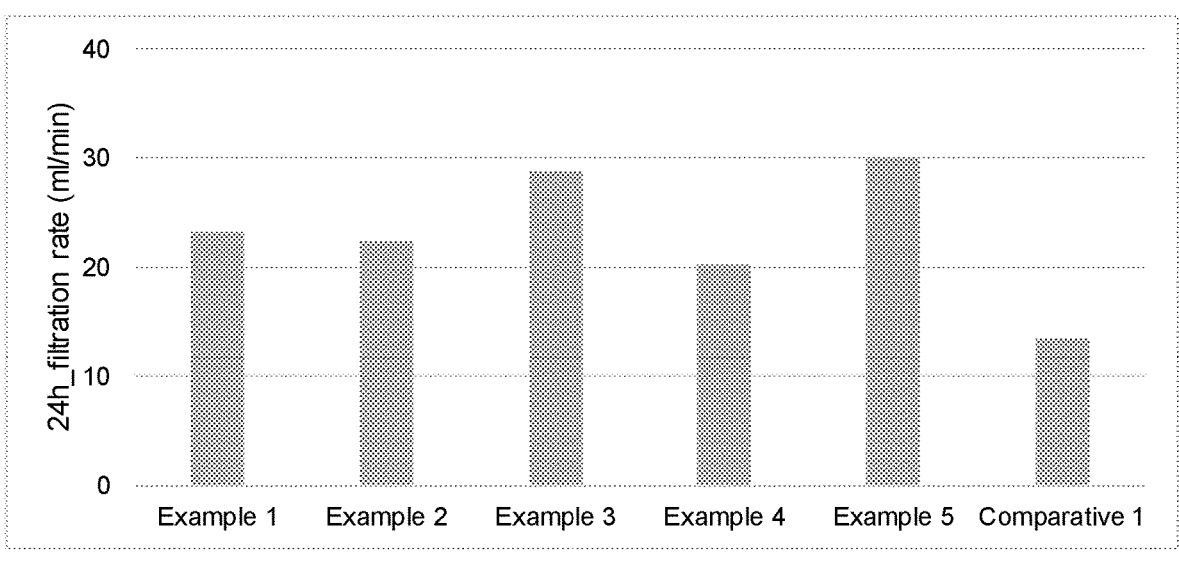
FIG. 3 shows a plot of comparison of filtration rate for sample after intensive attrition in $H_2O$ for 24h.
Figure 4:
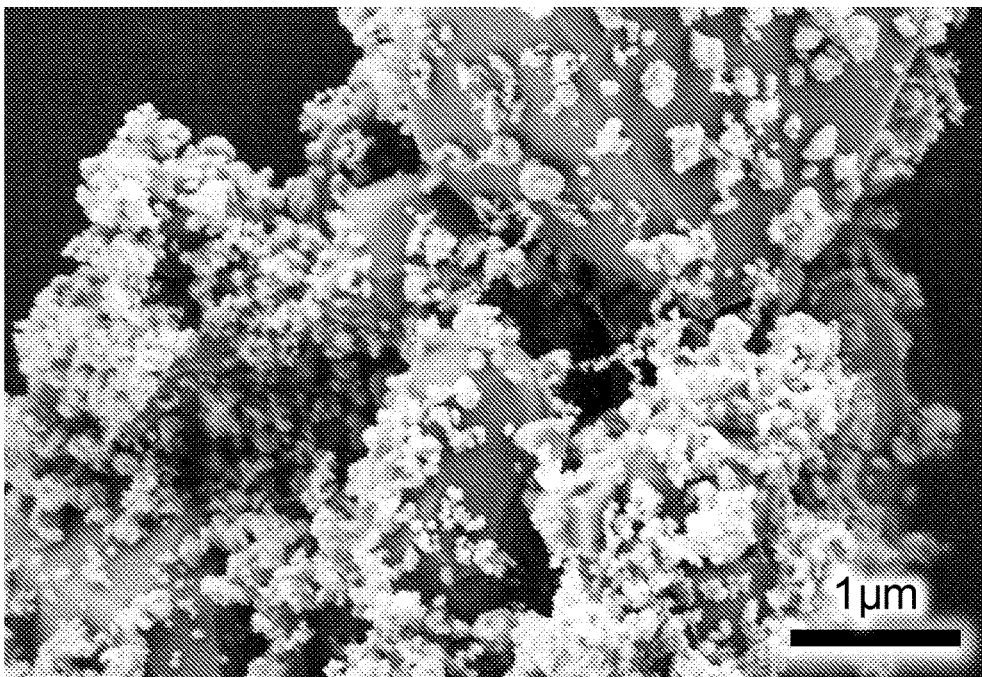
FIG. 4 shows the microstructure of the inventive catalyst.

Comparison of filterability for Examples and Comparative Examples was provided in FIG. 3. It is shown that less CuO or more alumina carrier in catalysts have positive effect on improving the filterability.

The invention claimed is:

1. A catalytic composition, comprising:
   5% to 35% by weight of Cu, calculated as CuO;
   0.1% to 7% by weight of Bi, calculated as $Bi_2O_3$; and
   60% to 95% by weight of Al, calculated as $Al_2O_3$.

2. The catalytic composition according to claim 1, wherein a Cu to Bi molar ratio is 55-300:1.

3. The catalytic composition according to claim 2, wherein a Cu to Bi molar ratio is 80-200:1.

4. The catalytic composition according to claim 1, wherein the catalytic composition comprises 10% to 30% by weight of Cu, calculated as CuO.

5. The catalytic composition according to claim 1, wherein the catalytic composition comprises 0.2% to 4% by weight of Bi, calculated as $Bi_2O_3$.

6. The catalytic composition according to claim 1, wherein the catalytic composition comprises 70% to 90% by weight of Al, calculated as $Al_2O_3$.

7. The catalytic composition according to claim 1, wherein the $Al_2O_3$ has a $D_{50}$ of 0.1 to 20 μm.

8. The catalytic composition according to claim 6, wherein the Al2O3 has a $D_{50}$ of 0.2 to 15 μm.

9. The catalytic composition according to claim 1, wherein the catalytic composition has a $D_{50}$ of 0.5 to 40 μm.

10. The catalytic composition according to claim 9, wherein the catalytic composition has a $D_{50}$ of 1 to 30 μm.

11. A process for producing a catalytic composition according to claim 1 comprising:
   1) precipitating an acidic copper-containing aqueous solution with precipitation agent, on a particulate carrier; and
   2) drying the treated particulate carrier and calcining at 300 to 800° C. to form the catalytic composition;
   wherein the particulate carrier comprises alumina.

12. A process for hydrogenation, dehydrogenation, hydrogenolysis, or ethynylation comprising reacting in the presence of the catalytic composition according to claim 1.

* * * * *